(12) United States Patent  
Bradica et al.

(10) Patent No.: US 9,017,417 B2  
(45) Date of Patent: Apr. 28, 2015

(54) SUBCHONDRAL BONE REPAIR SYSTEM (75) Inventors: Gino Bradica, Mullica Hill, PA (US); Timothy A. Ringeisen, Exton, PA (US)

(73) Assignee: Kensey Nash BVF Technology LLC, Wilmington, DE (US)

( * ) Notice: Subject to any disclaimer, the term of this patent is extended or adjusted under 35 U.S.C. 154(b) by 0 days.

(21) Appl. No.: 13/484,270

(22) Filed: May 30, 2012

(65) Prior Publication Data

US 2013/0325126 A1 Dec. 5, 2013

(51) Int. Cl.
- *A61F 2/02* (2006.01)
- *A61F 2/28* (2006.01)
- *A61F 2/30* (2006.01)
- A61F 2/46 (2006.01)

(52) U.S. Cl.
CPC ............... *A61F 2/2846* (2013.01); *A61F 2/28* (2013.01); *A61F 2/30756* (2013.01); *A61F 2002/2839* (2013.01); *A61F 2002/30163* (2013.01); *A61F 2002/30166* (2013.01); *A61F 2002/30289* (2013.01); *A61F 2002/30841* (2013.01); *A61F 2002/30897* (2013.01); *A61F 2002/4631* (2013.01)

(58) Field of Classification Search
USPC .......... 623/14.12, 18.11, 20.32, 23.47–23.48, 623/23.5–23.51, 23.56–23.63, 16.11, 623/23.47–23.48, 23.5–23.51, 23.56–23.63, 623/23.76; 606/80, 82, 79, 86 R, 87, 88, 89
See application file for complete search history.

(56) References Cited

U.S. PATENT DOCUMENTS

| | | | |
|---|---|---|---|
| 5,037,437 A * | 8/1991 | Matsen, III | 128/898 |
| 5,343,877 A * | 9/1994 | Park | 128/898 |
| 6,387,693 B2 | 5/2002 | Rieser et al. | |
| 6,620,185 B1 | 9/2003 | Harvie et al. | |
| 7,468,075 B2 | 12/2008 | Lang et al. | |
| 7,618,451 B2 | 11/2009 | Berez et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,083,745 B2 | 12/2011 | Lang et al. | |
| 8,105,330 B2 | 1/2012 | Fitz et al. | |
| 8,147,559 B2 | 4/2012 | Tallarida et al. | |
| 8,292,968 B2 | 10/2012 | Truncale et al. | |
| 2001/0039455 A1 * | 11/2001 | Simon et al. | 623/23.51 |
| 2003/0055502 A1 | 3/2003 | Lang et al. | |
| 2007/0198022 A1 | 8/2007 | Lang et al. | |
| 2009/0306676 A1 | 12/2009 | Lang et al. | |
| 2009/0312805 A1 | 12/2009 | Lang et al. | |
| 2009/0319045 A1 | 12/2009 | Truncale et al. | |
| 2010/0160917 A1 | 6/2010 | Fitz et al. | |

(Continued)

*Primary Examiner* — Yashita Sharma (74) *Attorney, Agent, or Firm* — Jeffrey R. Remberg (57) ABSTRACT

This invention includes a subchondral bone repair system, comprising a structural component and a fluid settable component and an optional non-core component. The fluid settable component may penetrate into any pores of the structural component, and set to a solid, thereby fixing the structural component in place. The fluid settable component will penetrate interporously into the pores of the subchondral bone tissue surrounding the device, beneficially displacing any fluid to reduce edema in the affected bone region. Furthermore, the settable component, once solid is osteoconductive to promote repair and regrowth of bone in the affected region, and will also transmit mechanical force stimuli (such as compressive forces) directed through the structural component, into the adjacent bone tissue, thereby providing appropriate force stimuli necessary for appropriate tissue growth.

3 Claims, 6 Drawing Sheets

(56) References Cited

U.S. PATENT DOCUMENTS

| | | |
|---|---|---|
| 2010/0168754 A1 | 7/2010 | Fitz et al. |
| 2010/0247651 A1 | 9/2010 | Kestler et al. |
| 2010/0303313 A1 | 12/2010 | Lang et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2011/0066193 A1 | 3/2011 | Lang et al. |
| 2011/0070271 A1 | 3/2011 | Truncale et al. |
| 2011/0071581 A1 | 3/2011 | Lang et al. |
| 2011/0125265 A1 | 5/2011 | Bagga et al. |
| 2011/0166669 A1 | 7/2011 | Truncale et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0295329 A1 | 12/2011 | Fitz et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0197260 A1 | 8/2012 | Fitz et al. |

* cited by examiner

*Prior Art*

SUBCHONDRAL BONE REPAIR SYSTEM

BACKGROUND OF THE INVENTION

The present invention is directed to a device and methods for repairing and replacing lost or damaged tissue. Particularly, the present invention is directed to the repairing or replacing of subchondral bone located below cartilage or cartilage-like tissues. The invention provides for the use of prosthetic devices which may be used as articular cartilage substitution material and as a scaffold for regeneration of damaged bone associated with articular cartilaginous tissues.

Cartilage is found throughout the body, such as in the supporting structure of your nose, ears, ribs (elastic cartilage), within the meniscus (fibrous cartilage), and on the surfaces of joints (hyaline cartilage or articular cartilage). A joint is a bending point where two bones meet. The knee, hip, and shoulder are the three largest joints.

The specialized covering on the ends of bones that meet to form an articulating joint is called hyaline or articular cartilage. It is the cartilage that is initially damaged and wears as we age, or sustain an injury followed by damage to the subchondral bone. Articular cartilage is unique amongst the body tissues in that it has no nerves or blood supply. This means that damage will not be felt until the covering wears down to bare underlying bone. Bone is very sensitive and the sharp pain of arthritis often comes from irritation of bone nerve endings and since human tissue has a very limited capacity to heal without a blood supply, articular cartilage cannot repair itself effectively. Thus the underlying bone remains exposed.

Articular cartilage tissue covers the ends of all bones that form diarthrodial joints. The resilient tissues provide the important characteristic of friction, lubrication, and wear in a joint. Furthermore, it acts as a shock absorber, distributing the load to the bones below. Without articular cartilage, stress and friction would occur to the extent that the joint would not permit motion. As stated above, articular cartilage has only a very limited capacity to regenerate. If this tissue is damaged or lost by traumatic events, or by chronic and progressive degeneration, it usually leads to tissue damage in the underlying bone, painful arthrosis and decreased range of joint motion.

Articular cartilage and subchondral bone repair following injury or degeneration represents a major clinical problem, with treatment modalities being limited and joint replacement being regarded as appropriate only for the older patient. In the surgery for joint replacement, the cartilage bearing surfaces, along with the immediate underlying subchondral bone region of the bones are removed entirely. The artificial implant is placed over the exposed bone while extending into the intermedullary canal of the bone, frequently being held in place with a cement, however there is no subchondral bone remaining to be treated, In contradistinction, the practice with the present invention requires the repair and regrowth of the bone tissue underlying the cartilage region (the subchondral bone), Current treatments for articular cartilage damage are varied and include anti-inflammatory medication, viscosupplementation, arthroscopic chondroplasty, autogenous articular cell implantation, microfracture and osteochondral articular transplantation. However, these procedures do not address issues with the underlying bone.

Anti-inflammatory medication: Aspirin was the first anti-inflammatory medication in the world. This was followed in 1950 by cortisone, a steroidal medication, used orally or by injection. Extensive use of cortisone has a wide variety of harmful effects, including having been associated with increased cartilage degradation. Later the non-steroidal drugs, such as ibuprofen were developed, which while considered to be safer than aspirin and cortisone, presented potent side effects, especially causing bleeding within the stomach and intestinal ulcers. These complications led to the development of the COX-2 inhibitor drugs, Celecoxib and Rofecoxib (marketed as Celebrex and Vioxx, respectively). While thought to be much safer and seemingly more effective, Vioxx was found to have significant cardiac side effects and is no longer available. With certain precautions, Celebrex is still widely used. However, these anti-inflammatory medications only treat the symptoms of cartilage damage and arthritis and do not promote repair.

Viscosupplementation: Viscosupplementation is a procedure that involves the injection of hyaluronan based materials into a joint to supplement the viscous properties of synoval fluid. Currently, hyaluronate injections are approved for the treatments of osteoarthritis of the knee in those who have failed to respond to more conservative therapy. Once again, this procedure only treats the symptoms of cartilage damage and arthritis and does not promote repair.

Arthroscopic chondroplasty: Chondroplasty is a term referring to the arthroscopic smoothing of unstable articular surfaces either with mechanical shaving or thermal devices. While not a restorative measure, so called debridement can be useful in reducing irritating cartilage debris that breaks off in the joint or causes catching or grinding sensations. The resulting improvement in the control of inflammation can last for several years. But this is not a final solution as the degenerative process continues to wear away at the articular cartilage.

Autogenous articular cell implantation (ACI): Autogenous cell implantation can be used for large, shallow defects, which do not involve the subchondral bone. In this procedure, cartilage cells collected from the patient and grown through cell culture techniques to a desired cell density are injected into the joint, under a membrane that has been attached to the cartilage surface. Although the ACI procedure has been proven successful when employed properly, the window of opportunity for this procedure is often missed, as the few clinical symptoms showing the need for ACI treatment are not evident until the defect deepens to involve the underlying bone, thus the damage encountered upon detection is frequently too extensive for repair through ACI techniques.

Microfracture: The goal of this arthroscopic technique is to improve the blood supply to the bare areas of the joint by creating tiny perforations in the underlying bone. The resulting bone marrow bleeding carries powerful growth stimulating factors found in platelets, as well as stem cells, to the damaged area, thereby creating what is referred to as a "super-clot". Healing and repair follow over several weeks. Studies have shown that microfracture techniques do not fill in the chondral defect fully and the repair material formed is fibrocartilage. The fibrocartilage tissue can temporarily return function for activities such as running and a sport play, but ultimately fails, as fibrocartilage is unable to mechanically share and dissipate loading forces as effectively as the original hyaline cartilage. Fibrocartilage is much denser and isn't able to withstand the demands of everyday activities as well as hyaline cartilage and is therefore at higher risk of breaking down.

Osteochondral articular transplantation: Osteochondral transplantation (i.e. mosaioplasty) involves transportation of tissue plugs from one location of the knee to another. Special instrumentation has been devised to harvest plugs of articular cartilage and its supporting bone from the patient's own joint. The harvested tissue is then transported to the damaged site where it is inserted into surgically created defects. Several plugs can together fill up rather large defects and will grow to re-supply a new joint surface. Unfortunately, this procedure leaves defects of equal or worse proportions elsewhere and often the harvested tissue is not viable due to the traumatic harvesting procedure.

Due to the problems associated with current state of the art treatments, much work has been done to produce a synthetic off-the-shelf scaffold to be used in place of the harvested osteochondral plug.

Originally, single-phase scaffolds of uniform construction were contemplated for use as implants. However, these single-phase scaffold implants proved unsuccessful in healing of the complex multi-phasic articular cartilage along with the underlying bone. Soon biphasic and then gradient devices were developed that were either mechanically or anatomically specific for the tissues involved. While these showed an improvement over single phase devices, it is evident that these devices do not take into consideration how cells will be migrating into the scaffolds as well as how their presence influences the surrounding, uninvolved cartilage and bone tissue. Additionally, prior art scaffolds did not take into consideration the joint fluid and how it impacts maturation and maintenance of healthy hyaline cartilage. Although prior art synthetic scaffolds, whether single phase, multi-phase, or of gradient construction have proven suitable for growth and maturation of cells within a bioreactor, these prior art devices are not suited for treating the area beyond the surgically created defect, for at least the reasons that follow.

Within the bone layer, prior art devices failed to recognize the impact a rigid scaffold has on the surrounding uninvolved tissue. Whereas malleable elastic scaffolds (scaffolds that can be deformed and then return to their original shape) are desirable for the cartilage layer, rigid stable scaffolds (scaffolds that resist deformation) are required for proper migration and attachment of bone forming cells. However, nearly the opposite conditions are required for stability of existing bone. Micro-motion and/or stresses are necessary to keep healthy bone from becoming osteopenic. Osteopenia refers to bone mineral density that is lower than normal. Bone mineral density has been shown to drop in healthy individuals who are bedridden, as well as in astronauts who have reduced stress on their skeletal system due to the effects of reduced gravity while in space. As this occurs, the bones lose minerals, heaviness (mass), and structure, making them weaker and increasing their risk of collapse and or breaking Localized bone mineral density loss has been witnessed due to stress shielding caused by orthopedic rods and plates. During repair of damaged cartilage with prior art devices, edema, voids and osteopenic zones form below and around the implanted tissue scaffolds. The theory behind this pathology formation is that stress shielding, caused by the presence of porous tissue scaffolds, results in bone density loss. This is believed to occur as the prior art biphasic scaffolds dampen vibrations that would normally be transferred through the malleable elastic articular cartilage phase to the calcified region phase, and then conducted into the surrounding bone. These conductive forces are necessary for normal bone biology. Additionally, bone edema, whether as a result of either the surgical procedure, or the initial pathology, will prevent suitable contact between the scaffold and surrounding bone, preventing integration. As the pressure from the bone edema continues, it can lead to interruption of blood supply and ultimately osteonecrosis. Osteonecrosis (also known as avascular necrosis, bone infarction, aseptic necrosis, ischemic bone necrosis, and AVN) is a disease where there is cellular death (necrosis) of bone components due to interruption of the blood supply. Without blood, the bone tissue dies and the bone collapses, thereby creating a void. Osteonecrosis involving the subchondral bone of a joint often leads to destruction of the joint articular surfaces. As the damaged bone is reabsorbed by the body, it leaves the auricular cartilage unsupported and prone to damage. The result is fragmentation of both cartilage and bone, and the free movement of these osteochondral fragments within the joint space, causing pain, further damage and ultimately the need for a total joint replacement.

In order to prevent undesirable bone voids from forming in uninvolved tissues adjacent to the repair device, what is needed is a scaffold capable of transferring forces through the device, and into the tissue. This deep bone mechanical stimulation can only occur if the repair scaffold itself is physically connected to the surrounding bone so as to promote mechanical stimulation and reduce bone edema. The fluid buildup that defines the bone edema, and may result in healthy bone becoming osteopenic, can be encouraged to diffuse away due to micro-motion and stresses seen in normal healthy bone.

SUMMARY OF THE INVENTION

What is needed is a novel device, capable of being implanted into the underlying bone of an articular cartilage lesion that has been surgically created, presenting a bone void region and a cartilage void region. This device must not only fill the bone void region under the cartilage void region, but also penetrate into the host bone surrounding the bone void region, thereby creating a bond between the device and the surrounding bone, and promoting cellular ingrowth into the device. Additionally, the penetration into the surrounding bone may serve to displace any bone edema fluids resulting from the surgical procedure, as well as prevent fluid edema from being able to form in the area of penetration. This host bone penetrating bond also is capable of transmitting mechanical stimuli back and forth between the device and the surrounding bone. For at least the reasons described above: 1) the device may prevent edema formation in the bone tissue adjacent to, and especially below the implant, 2) the device may transmit the mechanical forces stimuli necessary for appropriate tissue growth, and 3) the device may penetrate into the surrounding bone void tissue to promote cellular ingrowth of bone tissue, thus the device will effect the repair and regrowth of subchondral bone.

Thus in one embodiment, the device of the current invention has a structural core component for placement within the bone void region and a settable fluid component for placement within said bone void region, wherein the fluid component partially penetrates into the bone surrounding the bone void region after placement but prior to setting. This allows the device to be locked into the bone void. The two components may be combined prior to, or after being inserted into the surgically created tissue void.

The settable fluid component can penetrate, at least partially, into the interconnected porous network of the host bone surrounding the defect via multiple processes, such as injection through a needle or cannula, or displacement resulting from the placement of the structural core component. This displacement can occur when the structural core component is inserted into the bone void, forcing the settable fluid into the porosity of the surrounding bone resulting in interporous penetration (between pores) of the settable fluid, such that the settable fluid substantially fills not only those pores adjoining the defect site, but rather the settable fluid continues flowing into adjoining, interconnected pores of the subchondral bone. This interporous penetration is distinguishable from intraporous penetration, that is, flow that merely forms an interference fit, by extending at least partially into only the pores lining the defect site, without penetrating into the pores removed from the defect site. The interporous penetration is necessary to properly ensure the healing of bone tissue underlying and adjacent to the defect, such as by treating edema, or encouraging osteoconductive growth into the region. At the same time, should the structural core component present with features such as groves, indentations, cavities, projections or porosity, the settable fluid component may also penetrate around and into these features of the structural core component, to cause interlocking between the structural core component and the settable fluid component. For example, it is known in the art to employ a textured implant surface, such as by sintering metallic beads or fibers to the outside surface of a solid implant, where the textured surface allows cellular and tissue attachment to the irregular surface, without cellular penetration into the implant. Furthermore, as discussed with reference to the bone tissue above, the penetration into the pores of the structural component may be interporous penetration, in order to provide for secure fixation (due to the interdigitation of the settable fluid component with the surrounding tissue) of the structural component into the bone tissue, but also to promote osteoconduction into the structural component, to ensure integration of the implanted device into the healing tissue.

Additional ways for the settable fluid component to interface and/or penetrate the structural core component and the porosity of the surrounding bone is through expansion. Heat, gas formation or decompression of all or part of the settable fluid component can generate forces that drive the settable fluid around and into the structural core component and porosity of the surrounding bone.

The fluid settable component can set up and form a porous matrix capable of transmitting mechanical stimulus from the bone void into the surrounding bone or from the surrounding bone into the bone void and ultimately into the structural core component. In an alternative embodiment, the settable component may form a non-porous matrix, which may beneficially incorporate an additive, such as a porosifying agent, that would later result in the formation of pores in the matrix, thereby promoting osteoconduction. Mechanical stimulus transfer, also known as mechano-transduction, is known to provide positive influence on newly forming bone.

The fluid settable component can be formed from natural polymers, synthetic polymers, hydrogels, ceramic settable bone void filler or combinations of the four. The fluid settable component may also contain an adhesive component to improve the bond with the structural core component and or the surrounding host bone. When formed from a polymer, the settable fluid component may be dissolved or suspended in a solvent wherein the solvent diffuses away to induce setting. Alternatively, the polymer may be in a monomeric form that polymerizes or cross-links to induce setting. If the polymer cross-links, it may be the result of a true cross-link wherein a bond is formed between polymer molecules, or an end-capping or additive process, wherein a cross-linking material is added to the polymer, thus reducing its solubility and thus inducing setting as the polymer comes out of solution. The polymers may also form hydrogels, such at polyelectrolitic complexes (PEC's) that come out of solution as they form. The settable fluid components suitable for use in the present invention must be biocompatible, and osteoconductive, further, either while being delivered, or while setting by undergoing a phase change from a liquid to a solid, the settable component must remain biocompatible, for example, it remains at a temperature that is not harmful to the nearby tissues. For example, there are cements and polymers that in the course of the transition to a solid from a liquid, will be at a temperature that is able to cause cellular damage, these types of settable components are preferably avoided.

In another embodiment the settable fluid component is calcium phosphate cement. Calcium phosphate cement (CPC) is the generic term to describe chemical formulations in the chemical system $CaO-H_3PO_4-H_2O$ that can experience a transformation from a liquid or paste state to a solid state, and in which the end-product of the reaction is a calcium phosphate. These are not to be confused with cements such as poly-methyl methacrylate, which while a cement, does not result in an osteoconductive material. The cements contemplated for use in the present invention must be osteoconductive, that is they encourage ingrowth of bone cells into the material. CPCs consist generally of a concentrated mixture of one or several calcium phosphate powders and an aqueous solution (e.g. water), but it may also consist of a mixture of two or more solutions. CPC are bioactive bone substitute materials with unique properties for bone regeneration, due to their injectability and in vivo setting ability. CPC are hydraulic cements, which means that water is used as the liquid phase, and their hardening is not due to a polymerisation reaction, but to a dissolution and precipitation process. CPC have the capacity to form a direct bonding with bone, and they are osteoconductive materials. Moreover, they can be resorbable, with a resorption rate which depends on their composition and microstructural features. CPC were discovered by Legeros, Brown and Chow in the early 1980's. They demonstrated the formation of hydroxyapatite in a monolithic form at room or body temperature by means of a cementitious reaction. This was an important breakthrough in the field of bioceramics research, since it supplied a material which was moldable, and therefore could adapt to the bone cavity, presenting a good fixation and an optimum tissue-biomaterial contact, necessary for stimulating the bone ingrowth. Since then, calcium phosphate cements have attracted much attention and different formulations have been put forward. Currently many commercial products exist on the market. However, these commercial products are frequently used in joint replacement surgery, where the cartilage and chondral bone region is removed entirely, and the implant is fixed with a cement in an intermedullary canal, thus not effecting the repair and regrowth of the subchondral bone, as is taught herein. In the use for joint replacement, the cements is required to conform to a bone cavity or void rather than penetrate into, and through the pores of the surrounding uninvolved bone. In contradistinction, the use of the cement along with the structural component, as taught herein, features the penetration of the cement into the porous matrix of the bone, thus providing a benefit in use for subchondral repair, as in penetrating into the bone, the cement may serve to prevent fluid edema by displacing fluid from damaged bone tissue so that edema formation is interrupted, and the bone tissue is able to be repaired.

In another embodiment the settable fluid component also contains additives such as biologically active agents and/or particulates and combinations thereof.

Examples of Biologically Active Agents can be found in table 1.

TABLE 1

| Examples of Biological Active Ingredients |
| --- |
| Alcohol |
| Amino Acids |
| Angiogenic agents |
| Anti-bacterial agents |
| Antibiotics |
| Anti-coagulants |
| Anti-growth factors |

TABLE 1-continued

Examples of Biological Active Ingredients

Anti-inflammatory agents
Antioxidants
Anti-platelet agents
Anti-proliferation agents
Anti-rejection agents
   Rapamycin
Bacteria
Blood clotting factor
Bone morphogenic proteins (BMP)
Cells & Cellular materials
   Adipose cells
   Blood cells
   Bone marrow
   Cells with altered receptors or binding sites
   Endothelial Cells
   Epithelial cells
   Fibroblasts
   Genetically altered cells
   Glycoproteins
   Growth factors
   Lipids
   Liposomes
   Macrophages
   Mesenchymal stem cells
   Progenitor cells
   Reticulocytes
   Skeletal muscle cells
   Smooth muscle cells
   Stem cells
   Vesicles
Chondroitin Sulfate
Cytokines prostaglandins
Genetic material
Glycosaminoglycans
Growth factor antagonists or inhibitors
Growth factors
   Bone morphogenic proteins (BMPs)
   Core binding factor A
   Endothelial Cell Growth Factor (ECGF)
   Epidermal growth factor (EGF)
   Fibroblast Growth Factors (FGF)
   Hepatocyte growth factor (HGF)
   Insulin-like Growth Factors (e.g. IGF-I)
   Nerve growth factor (NGF)
   Platelet Derived Growth Factor (PDGF)
   Recombinant NGF (rhNGF)
   Tissue necrosis factor (TNF)
   Transforming growth factors alpha (TGF-alpha)
   Transforming growth factors beta (TGF-beta)
   Vascular Endothelial Growth Factor (VEGF)
   Vascular permeability factor (UPF)
   Acidic fibroblast growth factor (aFGF)
   Basic fibroblast growth factor (bFGF)
   Epidermal growth factor (EGF)
   Hepatocyte growth factor (HGF)
   Insulin growth factor-1 (IGF-1)
   Platelet-derived endothelial cell growth factor (PD-ECGF)
   Tumor necrosis factor alpha (TNF-.alpha.)
Growth hormones
Heparin sulfate proteoglycan
Hormones
Interleukins
Morphogens
Nitric oxide (NO)
Nucleotides
Peptides
Proteins
Prostaglandins
Proteoglycans
Statins
Stem Cells
Steroids
Strontium
Thrombin
Vitamins
Yeast Examples of particulates can be found in Table 2.

TABLE 2

Examples of particulate materials

Alginate
Anorganic Bone
Bioglass
Calcium
Calcium Phosphates
Calcium Sulfates
Ceramics
Chitin
Chitosan
Cyanoacrylate
Collagen
Dacron
Demineralized Bone
Elastin
ExtraCellular Matrix Tissues (ECM's)
Fibrin
Gelatin
Glass
Gold
Hyaluronic acid
Hydrogels
Hydroxy apatite
Hydroxyethyl methacrylate
Liposomes
Magnesium
Mesenchymal cells
Nitinol
Osteoblasts
Oxidized regenerated cellulose
Phosphate glasses
Polyethylene glycol
Polyester
Polymers (Natural & Synthetic)
Polysaccharides
Polyvinyl alcohol
Platelets, blood cells
Radiopacifiers
Salts
Silicone
Silk
Steel (e.g. Stainless Steel)
Sulfates
Synthetic polymers
Thrombin
Titanium The structural core component may completely fill the bone void region or may only partially fill the bone void region. The structural core component may be solid, hollow, porous or a combination of the three. It is also envisioned that the structural core component may extends at least partially up into the cartilage void region. In this way host cartilage may grow over the top of, or partially into the structural core component. Additionally, the structural core component may completely fill the cartilage void regions, thus taking the place of the missing cartilage, or it may reach to the top of the cartilage void region within the center of the void, not reaching the outer edges of the void. In this way, host cartilage can grow out to, and come into intimate contact with the structural core component and thus closing the cartilage void without having to completely fill the cartilage void region.

In the embodiment in which the structural core component is porous, the pores may be interconnected. Further, the settable component may be sufficiently fluid or flowable initially or at a first time that it flows into at least a portion of adjoining pores of the structural core component, as well as flowing substantially completely around the outside perimeter of the structural core component.

In another embodiment, the structural core component extends into the porosity of the bone. This preferably is at the base of the bone void, but can also be one or more point along the entire surface defining the bone void regions. These extension that reach into the bone may be hollow or solid in form and may include bone engaging features, such as threads, barbs, ridges or other features that resist dislodgement.

In another embodiment, the structural core component has an internal hollow channel with access holes that allow the settable fluid component to at least partially penetrate into the hollow channel. In another embodiment, said hollow channel can connected to a syringe, or a needle placed into it so that the settable fluid component can be injected into the hollow channel wherein it is expressed out of the access holes along the structural core thus filling the bone void region and at least partially penetrating into the porosity of the surrounding host bone.

In another embodiment the structural core component can present topographical features that allow the settable fluid component to lock onto the structural core component after setting. These topographical features can be regular or irregular in position as well as overall form. For example, the structural core may have projections that extend out from the central column that reach partially or completely to the surface of the bone void region, or may even serve as bone engaging features that penetrate into the porosity of the surrounding host bone. These bone engaging features may be projections that extend into the bone, in the form of barbs, screw threads or thread portions, or ridges, or other shapes as are known to those skilled in the art. The projecting bone engagement features may be solid or porous.

In another example, the structural core component may take on the form of a solid, hollow or porous screw wherein the screw wherein the threads of the screw drive the settable fluid component into the porosity of the bone when the structural core is twisted or screwed into place within the bone void region.

In another embodiment, the structural core component is in the form of multiple segments, rods, plates, or large particulates that becomes embedded within said settable fluid component.

The structural core component can be composed of non-resorbable materials selected from the group consisting of polymers, metals, ceramics, glass, carbon or combinations thereof. Alternatively the structural core component can be composed of resorbable materials such as natural polymers, synthetic polymers, metals, ceramics, glass, bone, or combinations thereof. Additionally, the structural core component can contain additives such as biologically active agents and/or particulates.

In another embodiment there is a non-core component located on the top of the structural core component for location or placement within part or the entire cartilage void region. The non-core component may completely fill the cartilage void regions, thus taking the place of the missing cartilage, or it may only partially fill the cartilage void regions. For example in the form of a dome it may reach to the top of the cartilage void region within the center of the void, not reaching the outer edges of the void. In this way, host cartilage can grow out to, and come into intimate contact with the structural core component and thus closing the cartilage void without having to completely fill the cartilage void region with new cartilage tissue.

The non-core component can be rigid or malleable. Additionally, the non-core material may swell upon contact with fluids, and thus become malleable only upon hydration. The non-core component can be non-porous, or porous wherein cartilage cell migrate into the non-core component. Additionally, the non-core component can contain additives such as biologically active agents and/or particulates. The non-core component can be non-resorbable or resorbable and composed of material similar to those of the structural core component. Alternatively, the non-core component can be composed a material dissimilar to the structural core component such as cartilage tissue, ECMs, natural polymers, synthetic polymers, collagen, hydrogels, and combinations thereof In one embodiment the non-core component extends beyond the cartilage void region extending into the bone void region. Alternatively the non-core component may extend over the normal host cartilage.

In another embodiment there exists a multiphasic device for repair or replacement of articular cartilage and the underlying bone, this device presents a bone region and a cartilage region. The bone region is formed from a settable fluid component and a structural core component as defined above. It may also contain a cartilage region comprising a malleable component. The entire device may be implanted into a surgically created defect as a single device, or alternatively one component at a time. The settable fluid component penetrates beyond the surgically created defect into the surrounding host tissue prior to setting. In doing so, the settable fluid component displaces fluid edema and/or prevents fluid edema from forming and thus prevents bone voids from forming adjacent to the original created surgical defect.

Additionally, the settable fluid component of the multiphasic implant provides for the transmission or conduction of compressive forces through the device, down to the bone tissue surrounding the device; in this manner, bone tissue loss below the device, such as may occur due to stress-shielding, may be minimized or avoided.

The various embodiments described herein may be at least partially or completely resorbed by the living being. The various embodiments described herein may also feature drugs, biologically active agents, or other additives in all or at least a portion of the device.

Various medical uses of the above-described invention are described below. Other features or advantages of the present invention will be apparent from the following drawings and detailed description of the invention, as well as from the claims.

DETAILED DESCRIPTION OF THE INVENTION

Figure 1:
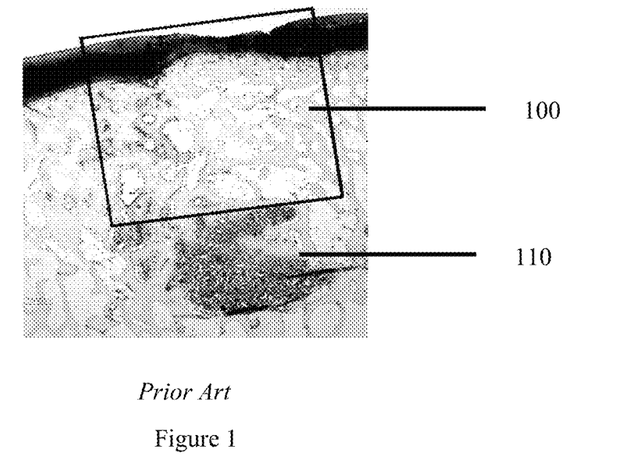
FIG. 1: Histology of poorly healed osteochondral defect.

FIG. 1 shows histology of a poorly healed osteochondral defect, which had been subjected to a repair by use of a prior art osteochondral repair device, characterized in that there was no settable bone void filler used in combination with the prior art implant device. Box 100 represents the original location of a previously implanted prior art osteochondral repair device. Notice large irregular void 110 directly under the location of the original treatment site. It is believed that voids 110 such as these that result from lack of mechanical stimulus and untreated fluid edema. It is the goal of the current invention to treat not only the original surgically created tissue defect, but also the surrounding host tissue that is traumatized by the surgical procedure, that results in tissue damaging fluid edema.

Figure 2A:
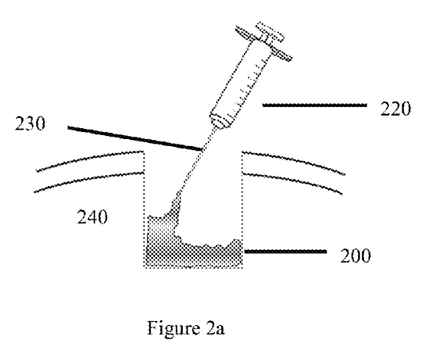
FIG. 2a: Syringe delivery of settable fluid component.
Figure 2B:
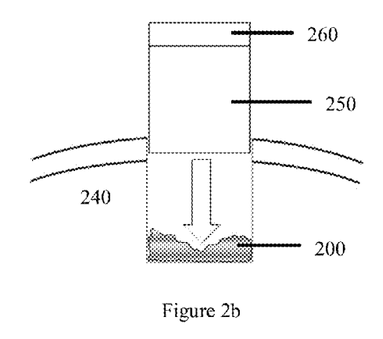
FIG. 2b: Insertion of structural core component having non-core component into settable fluid component.
Figure 2C:
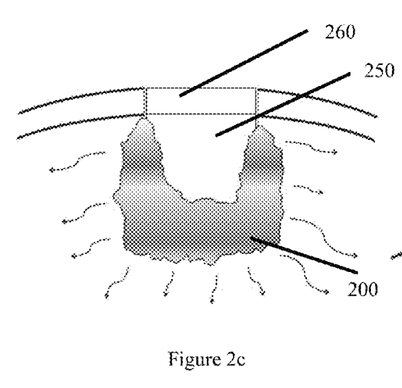
FIG. 2c: Migration of settable fluid core component into surrounding bone.
Figure 2D:
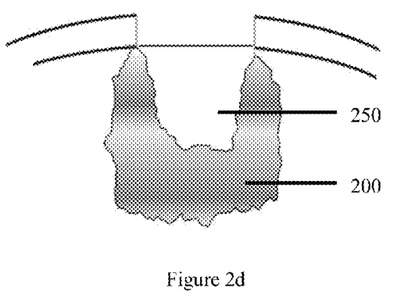
FIG. 2d: Device without non-core component.

FIGS. 2a, 2b and 2c show a sequence of events depicting the repair of an osteochondral defect, using an embodiment of the current invention. FIG. 2a shows delivery of fluid settable component 200 from syringe 220 through injection needle 230 into a surgically created tissue void. It is also envisioned that injection needle 230 could be employed to deliver the settable fluid component directly into the defect area, or alternatively, the needle may be inserted into one or more locations of surrounding host bone 240 to deliver the settable fluid component into the host tissue surrounding the surgically created tissue void. FIG. 2b shows insertion of structural core component 250 with attached non-core component 260 into a tissue void that has been partially filled with fluid settable component 200. FIG. 2c shows displacement of fluid settable component 200 by the insertion of structural core component 250, resulting in fluid settable component 200 being driven out from the defect site, into the surrounding host bone 240 as well as being displaced and forced to flow around structural core component 250. It is also envisioned that structural core component 250 may be porous, thus providing for the displaced fluid settable component 200 to be driven into the pores of the structural core component 250 at the same time the fluid settable component is being driven into surrounding host bone 240. To aid in migration of the fluid settable component 200 into host tissue 240, injection needle 230 shown in FIG. 2a can be used to fenestrate surrounding host bone 240. The flow of the settable component into the porous network of bone tissue surrounding the defect site may be particularly desirable to prevent the formation of edemas in the area surrounding the defect, as the settable component flows, it will tend to flow more readily towards tissue that has fluid build up, rather than healthy bone tissue (thus it is self-selective for damaged bone tissue), in this manner, the edema fluid is displaced by osteoconductive settable component, which will set to a solid and promote the repair of bone tissue. Structural core component 250 may fit tightly into the tissue void, or may leave a gap that is bridged by fluid settable component 200. Although it is envisioned that non-core component 260 shown in FIGS. 2b and 2c will be attached to structural core component 250, it is not required. FIG. 2d shows fluid settable component 200 and structural core component 250 without a non-structural core component. However, if desired, it is contemplated that a non-core component could be attached after structural core component 250 is inserted. FIGS. 3a, 3b, 3c and 3d show progressive healing and resorbtion of the device depicted in FIG. 2d.

Figure 3A:
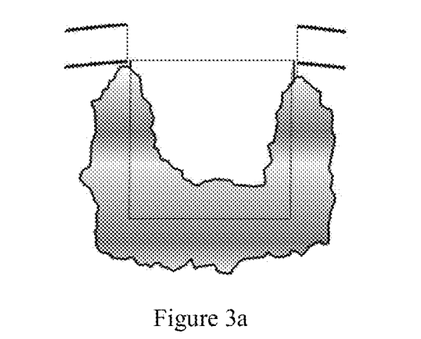
FIG. 3a-3d: Show progressive healing of a defect without non-core component.
Figure 3B:
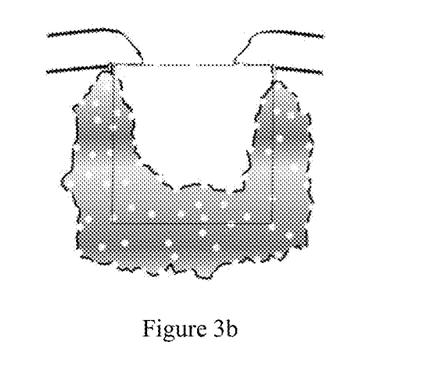
Figure 3C:
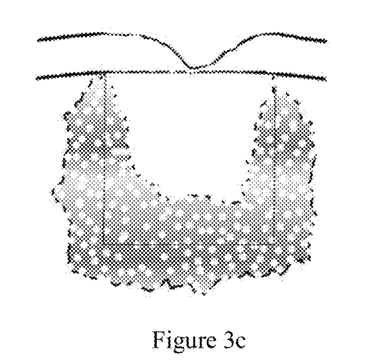
Figure 3D:
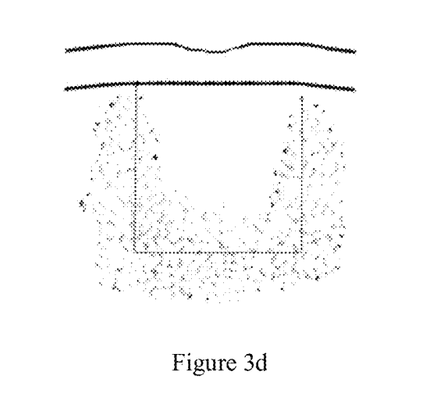

In the embodiment depicted in FIG. 2d, the device, without the inclusion of a non-core component, is implanted in a defect void. As there is no non-core component, there is initially a gap corresponding to the cartilage region at the exposed surface of the implant 250. As shown in the sequence of FIGS. 3a, b, c and d, the healing of the cartilage region may occur, concurrent with the resorption of the settable fluid component and establishment of bone tissue within the of the bone region of the device. As depicted in FIG. 3b, the healthy cartilage adjacent to the defect site will grow into the gap, and, as shown in FIG. 3c, the expanding healthy cartilage tissue continues to expand into the gap, and eventually covers completely the implant 250. This cartilage regrowth is enabled by the repair of the underlying bone. The bone repair is fostered by the osteoconduction of healthy bone cells into the osteoconductive settable fluid component. Upon setting to a solid phase, the settable component will now create the appropriate environment to support bone growth into the device itself, and also promote repair of the adjacent bone tissue. As discussed previously, the settable component also creates an osteoconductive environment, and transmits the necessary forces from the implant into the surrounding bone tissue, thereby preventing bone degradation due to stress shielding. Furthermore, due to the penetration of the settable fluid component into the adjoining pores of the surrounding tissue, the settable fluid component will tend to displace any fluid edema that may have occurred prior to, or during the repair procedure. In this manner, a healthy bone region surrounding the implant is provided for, as well as encouraging the subsequent ingrowth of healthy bone cells into the implant device itself, eventually restoring the normal bone tissue in the area of the treated defect. Concurrent with the restoration of healthy bone tissue in the defect site, the regrowth of normal cartilage into the gap area immediately above the bone defect site is occurring, eventually leading to the restoration of a layer of normal cartilage, as shown in FIG. 3d at the implant site. Thus as a result of the implant device providing for a stable bone foundation, at the implant site, and immediately surrounding the device, the regrowth of cartilage into the gap region is made possible. This type of cartilage restoration would not be possible where there is not a stable, healthy bone support underneath that would form the required stable foundation.

Figure 4A:
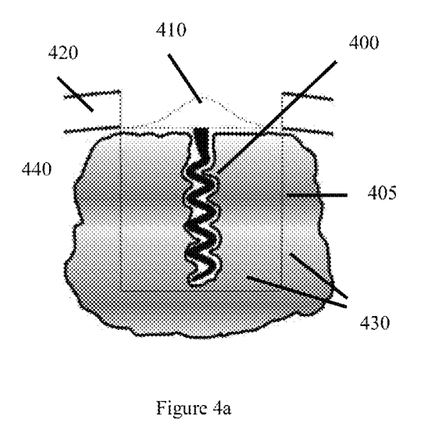
FIG. 4a-4c: Shows progressive healing around a non-degradable structural core component with a non-degradable non-core component.
Figure 4B:
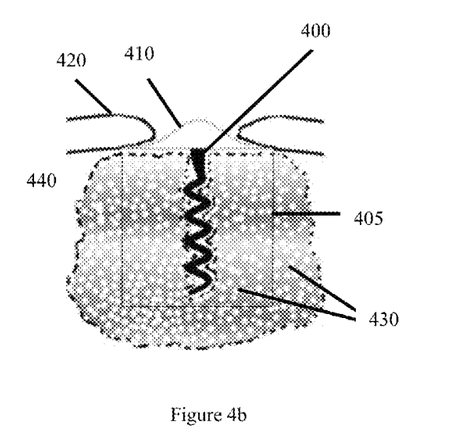
Figure 4C:
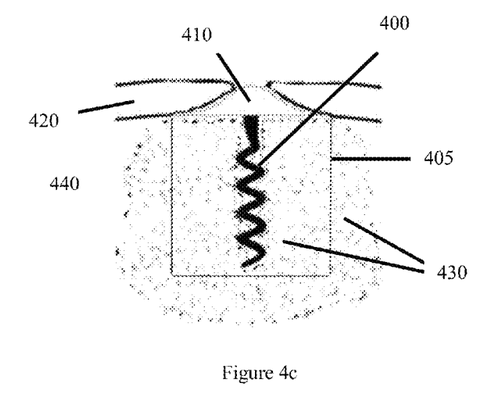

An alternative embodiment of the device is depicted in the sequence of FIGS. 4a, 4b and 4c showing the progressive healing around a non-degradable implant, here depicted as a cork screw shaped structural core component 400 placed within bone void region 405, defined by the rectangular box, of the surgically created tissue defect. Also shown is optional non-degradable non-core component 410 in the form of a dome in the center of cartilage tissue 420. Fluid settable component 430 flows around structural core component 400 and into surrounding host bone 440 prior to setting. As fluid settable component 430 resorbs, it is replaced by new bone. In another embodiment, not shown, the structural core component 400 penetrates and anchors itself into the host bone.

Figure 5:
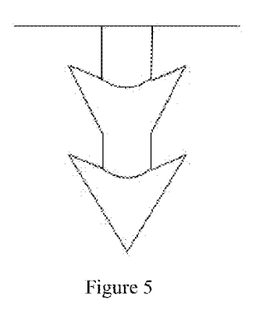
FIG. 5: Shows a structural core component is the form a barbed dart.
Figure 6A:
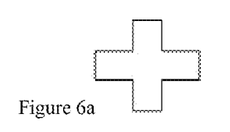
FIGS. 6a-6b: Shows a structural core component is the form of a cross beam.
Figure 6B:
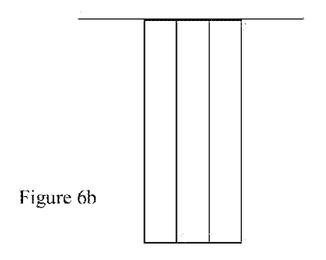
Figure 7A:
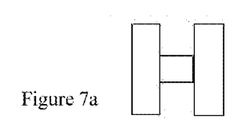
FIGS. 7a-7b: Shows a structural core component is the form an "I" beam.
Figure 7B:
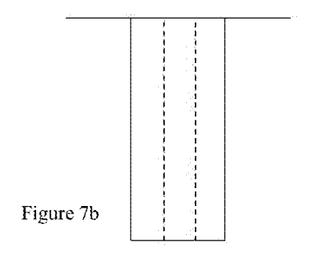
Figures 8, 9:
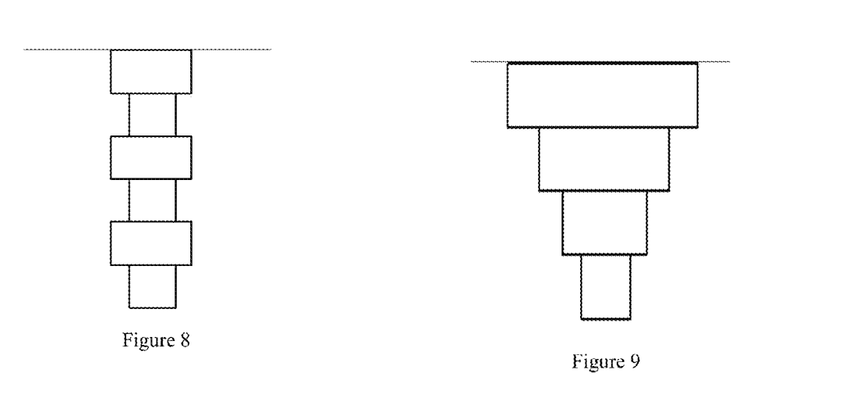
FIG. 8: Shows a structural core component is the form a banded rod.
FIG. 9: Shows a structural core component is the form a stepped cone/pyramid.

In addition to the cylindrical plug device, and the corkscrew shape shown in FIGS. 2, 3 and 4, the structural component may also be in other forms suitable for fasteners, such as in the form of a barbed dart as seen in FIG. 5; a cross, as seen in FIG. 6a (depicting the end-on view) and 6b; an "I" beam as seen in FIG. 7a (depicting the end-on view) and 7b; a banded rod as seen in FIG. 8; or a stepped cone/pyramid as see in FIG. 9. It is recognized that other device shapes could be substituted for another, such as a traditional screw, spear head or cone, that would be implanted in conjunction with the settable fluid component, as described herein. Still other shapes will be obvious to those skilled in the art. Also obvious to those skilled in the art is that all of the above described structural core components can be resorbable or non-resorbable, as well as porous or non-porous. Additionally, there may also be a non-core component attached to the top surface, for interfacing the cartilage region of a surgically created osteochondral tissue defect.

Other features or advantages of the present invention will be apparent from the following claims. Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all the changes which come within the meaning and range of equivalency of the claims are intended to be embraced therein.

What is claimed is:

1. A method for treatment of underlying bone of an articular cartilage lesion, said method comprising the steps of:
   a. providing a repair system comprising a structural: core component and a core component, and a settable component,
   b. creating a tissue void at the site of an articular cartilage lesion, said tissue void extending into the bone to create a bone void region and a cartilage void region;
   c. placing said settable corn orient into said tissue void wherein said settable component is initially in the form of a liquid, and wherein said setting is characterized by a phase change from a liquid to a solid, and further, wherein said solid is a osteoconductive matrix; and
   d. placing said structural core component into direct contact with said settable component in said tissue void;
   wherein, prior to said setting of said settable component, the placing of said structural core component is performed, and further, said settable component penetrates interporously not only into interconnected pores of the underlying bone surrounding the pone void region and adjacent said defect site, but also continues flowing into adjoining interconnected pores; and
   wherein the settable component is placed within the tissue void prior to placement of the structural core component, wherein the placement of the structural core component displaces the gettable component, whereupon the gettable component commences said penetration and continues flowing into adjoining interconnected pores.

2. A method for treatment of underlying bone of an articular cartilage lesion, said method comprising the step of:
   a. providing a repair system comprising a structural core component, and a settable component,
   b. creating a tissue void at the site of an articular cartilage lesion, said tissue void extending into the bone to create a bone void region and a cartilage region;
   c. placing said settable component into said tissue void, wherein said settable component is initially in the form of a liquid, and wherein said setting is characterized by a phase change from a liquid to a solid, and further, wherein said solid is a osteoconductive matrix; and
   d. placing said structural core component into direct contact with said settable component in said tissue void;
   wherein the settable component is placed within the tissue void prior to placement of the structural core component, and prior to said setting of said settable component, the placing of said structural core components is performed, wherein the placement of the structural core component displaces the settable component further, said settable component penetrates interporously into interconnected pores of the underlying bone surrounding the bone void region.

3. A method for treatment of underlying bone of an articular cartilage lesion, said method comprising the steps of:
   a. providing a repair system comprising a structural core component, and a settable component,
   b. creating a tissue void at the site of an articular cartilage lesion, said tissue void extending into the bone to create a bone void region and a cartilage void region;
   c. placing said settable component into said tissue void, wherein said settable component is initially in the form of a liquid, and wherein said setting is characterized by a phase change from a liquid to solid, and further, wherein said solid is a osteoconductive matrix; and
   d. placing said structural core component into direct contact with said settable component in said tissue void;
   wherein, the settable component is placed within the tissue void prior to placement of the structural core component, and prior to said setting of said settable component, the placing of said structural core components is performed, wherein the placement of the structural core component displaces the settable component and further, said settable component penetrates interporously into interconnected pores underlying bone surrounding the bone void region and adjoining said defect site, and furthermore penetrates into pores removed from said defect site.

* * * * *

UNITED STATES PATENT AND TRADEMARK OFFICE
CERTIFICATE OF CORRECTION

PATENT NO. : 9,017,417 B2  Page 1 of 1
APPLICATION NO. : 13/484270
DATED : April 21, 2015
INVENTOR(S) : Bradica et al.

It is certified that error appears in the above-identified patent and that said Letters Patent is hereby corrected as shown below:

In the Claims

Column 13, lines 19 and 20, delete ": core component and a"

Column 13, line 25, replace "com orient" with "component"

Column 13, line 36, replace "pone" with "bone"

Column 13, lines 42 and 43, replace each "gettable" with "settable"

Column 14, line 5, insert --void-- between "cartilage" and "region"

Column 14, line 28, replace "component further" with "component, and further"

Column 14, line 43, insert --of the-- between "pores" and "underlying"

Signed and Sealed this
Eighteenth Day of August, 2015

Michelle K. Lee
*Director of the United States Patent and Trademark Office*